Figure 1:
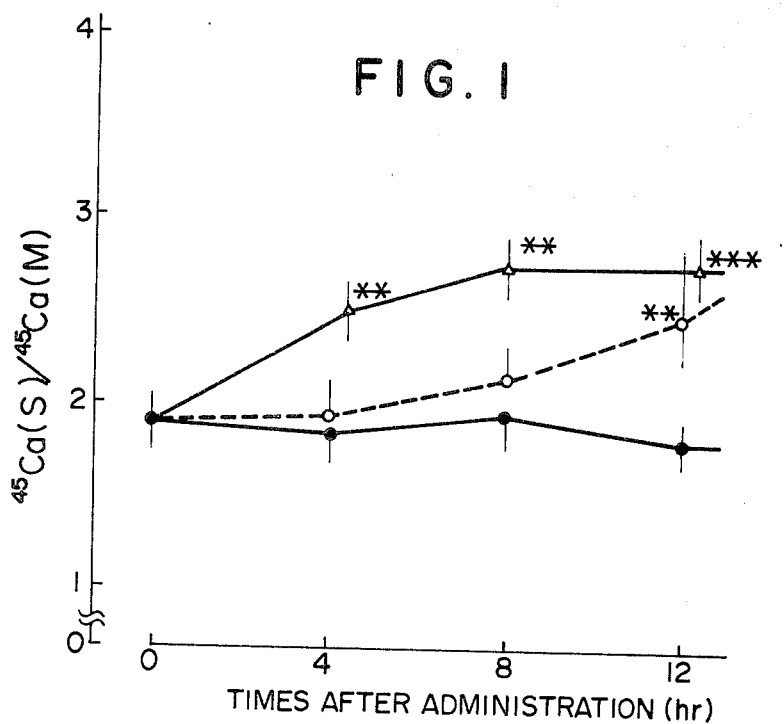

United States Patent [19]

Takeshita et al.

[11] 4,199,577

[45] Apr. 22, 1980

[54] NOVEL 1α-HYDROXY-24-OXOVITAMIN $D_3$, ITS PREPARING PROCESS AND THE NOVEL PRECURSORS THEREOF

[75] Inventors: Toru Takeshita; Takao Niki; Hiroyuki Kawashima; Kiyoshi Bannai, all of Hino, Japan

[73] Assignee: Teijin Limited, Osaka, Japan

[21] Appl. No.: 939,043

[22] Filed: Sep. 1, 1978

[30] Foreign Application Priority Data

Sep. 7, 1977 [JP] Japan .............................. 52-106677

[51] Int. Cl.$^2$ .............................................. C07J 9/00
[52] U.S. Cl. ................................. 424/236; 260/397.2
[58] Field of Search ...................... 260/397.2; 424/236

[56] References Cited

U.S. PATENT DOCUMENTS

| | | | |
|---|---|---|---|
| 3,833,622 | 9/1974 | Babcock et al. | 260/397.2 |
| 4,165,660 | 8/1978 | Jones | 260/397.2 |

*Primary Examiner*—Elbert L. Roberts
*Attorney, Agent, or Firm*—Sughrue, Rothwell, Mion, Zinn and Macpeak

[57] ABSTRACT

Novel 1α,3β-dihydroxy-24-oxocholesta-5,7-diene and the hydroxyl group-protected derivatives thereof.

Said novel 1α-hydroxy-24-oxovitamin $D_3$ and said novel intermediates are also useful as the intermediates of 1α,24-dihydroxyvitamin $D_3$.

1α,3β-Dihydroxy-24-oxocholesta-5,7-diene and the hydroxyl group-protected derivatives thereof are prepared from fucosterol via 1α,3β-diprotected hydroxy-24(24)-ethylenedioxycholest-5-ene. 1α-hydroxy-24-oxovitamin $D_3$ is prepared by irradiation with ultraviolet rays to 1α,3β-dihydroxy-24-oxocholesta-5,7-diene or a hydroxyl group-protected derivatives thereof, isomerization using heat energy, and, when necessary, elimination of the protecting groups.

7 Claims, 2 Drawing Figures

NOVEL 1α-HYDROXY-24-OXOVITAMIN D₃, ITS PREPARING PROCESS AND THE NOVEL PRECURSORS THEREOF

The present invention relates to novel 1α-hydroxy-24-oxovitamin $D_3$, the novel precursors thereof, 1α,3β-dihydroxy-24-oxocholesta-5,7-diene, or the hydroxyl group-protected derivatives thereof, and the process for preparing the novel 1α-hydroxy-24-oxovitamin $D_3$.

Further, the present invention relates to pharmaceutical compositions for warm-blooded animals containing effective amounts of the novel 1α-hydroxy-24-oxovitamin $D_3$, and a method of controlling the calcium metabolism of warm-blooded animals which comprises administrating a pharmaceutically effective amount of the novel 1α-hydroxy-24-oxovitamin $D_3$.

The novel 1α-hydroxy-24-oxovitamin $D_3$ is expressed by the following structural formula (2):

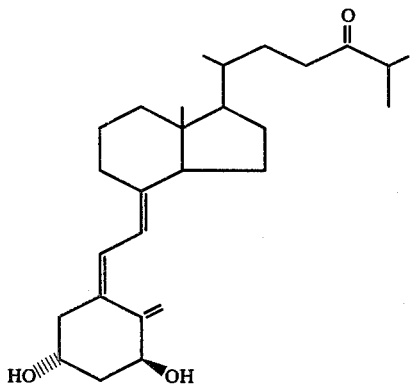

According to the works done by the present inventors, it has been found that the novel 1α-hydroxy-24-oxovitamin $D_3$ has high pharmaceutical effects as agent for controlling the calcium metabolism of warm-blooded animals and that the pharmaceutical effects are outstandingly superior to those of vitamin $D_3$, as illustrated in the detailed animal test described later in examples.

The 1α-hydroxy-24-oxovitamin $D_3$ in the present invention is a new compound that has never been described in any literature and the process for preparation and the biological activities thereof were unknown.

Namely, in the present invention it has been demonstrated that the structural feature of this novel vitamin $D_3$, that is, the presence of a hydroxyl group on 1α-position and an oxo group on 24 position, is reflected in more rapid intestinal calcium absorption and increased calcium concentration in blood and additionally, be reflected more marked effects exhibited in the bone resorption and remedy of rickets as compared with those of 1α,25-dihydroxy or 1α-hydroxy vitamin $D_3$.

The novel 1α-hydroxy-24-oxovitamin $D_3$ and the novel precursors, i.e., 1α,3β-dihydroxy-24-oxocholesta-5,7-diene or the hydroxyl group-protected derivatives thereof, are all useful also as intermediates for 1α,24-dihydroxy vitamin $D_3$ which was proposed previously by parts of the present inventors (refer to the specification of U.S. Pat. No. 4,022,891).

The present inventors have now succeeded in preparation of 1α-hydroxy-24-oxovitamin $D_3$ and the precursors thereof, which will be described in detail below.

The object of the present invention is to provide a process for preparing 1α-hydroxy-24-oxovitamin $D_3$ from 1α,3β-dihydroxy-24-oxocholesta-5,7-diene or the hydroxyl group-protected derivatives thereof of formula (1):

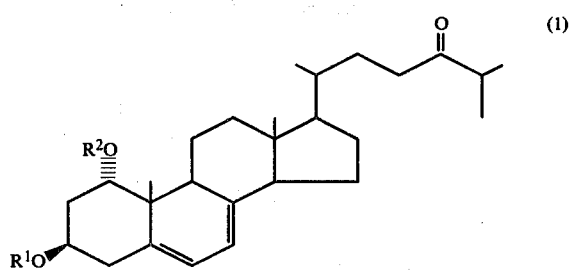

where $R^1$ and $R^2$ are same or different and represent hydrogen atom or hydroxyl-protecting group, through irradiation with ultraviolet rays to the compound in an inert organic solvent, followed by isomerization and, when necessary, elimination of the hydroxyl protecting groups.

The starting compound in the present invention, 1α,3β-dihydroxy-24-oxocholesta-5,7-diene or a derivative thereof can be readily prepared in high yield, for example by a route that was proposed previously by the present inventors, that is, from fucosterol via 24-oxocholesterol and 1α,2α-epoxycholesta-4,6-diene-3,24-dione-24-ketal. This process also has the great advantage over the process for preparing 1α,25-dihydroxycholesterol or 1α,3β,25-trihydroxycholesta-5,7-diene known as other intermediates for 1α,25-dihydroxy vitamin $D_3$.

Among 1α,3β-dihydroxy-24-oxocholesta-5,7-diene or the hydroxyl group-protected derivatives thereof of above formula (1), 1α,3β-diprotected hydroxy-24-oxocholesta-5,7-diene, where both $R^1$ and $R^2$ are hydroxyl protecting groups, is readily prepared by brominating 1α,3β-diprotected hydroxy-24-oxocholesta-5-ene-24-ketal into the allyl-brominated derivative, followed dehydrobromination and subsequent elimination of the protecting groups. The compound of formula (1) where both of $R^1$ and $R^2$ are hydrogen atoms can also be readily prepared by eliminating the protecting groups from the above diprotected hydroxy-5,7-diene derivative. In formula (1), $R^1$ and $R^2$ are same or different and represent hydrogen atom or a group for protecting hydroxyl group. As the hydroxyl group-protecting group, any group that is commonly used for protecting hydroxyl groups of cholesterols may be employed. Some of examples will be mentioned below.

(a) Acyl groups;

A residue of an aliphatic carboxylic acid having 1–12 carbon atoms, an aromatic carboxylic acid or the nitro, halogen, alkoxy-substituted derivative thereof is preferably used, for example, acetyl, propanoyl, butanoyl, pivaloyl, pentanoyl, chloroacetyl, bromoacetyl, benzoyl, p-bromobenzoyl, p-nitrobenzoyl, ethylbenzoyl or toluoyl group. Among them acetyl, benzoyl, propanoyl or pivaloyl group is much preferred.

(b) groups forming ether linkage with hydroxyl group;

For example, a trialkylsilyl group such as trimethylsilyl or dimethyl-t-butylsilyl, a cyclic ether group, such as 2-tetrahydropyranyl or 2-tetrahydrofuranyl group can be used.

Among above protecting groups, acyl groups are much preferred.

Thus, among 1α,3β-dihydroxy-24-oxocholesta-5,7-diene or the hydroxyl group-protected derivatives thereof that are used in the present invention and expressed by the formula (1), 1α,3β-diprotected hydroxy-24-oxocholesta-5,7-dienes of the following formula (1-a),

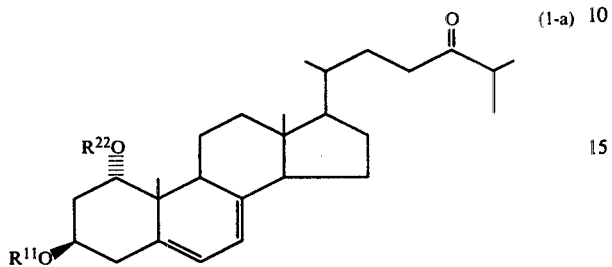

wherein $R^{11}$ and $R^{22}$ are same or different and each of them represents hydrogen atom, an acyl group having at least three carbon atoms, trialkylsilyl group or 2-cyclic ether group, are new compounds as far as the present inventors know. Therefore, another object of the present invention is to provide such useful precursors. Said novel precursors can be used not only as a starting material in the present invention but also as a useful intermediate for 1α,24-dihydroxyvitamin $D_3$ as described in Reference later.

In the present invention, 1α,3β-dihydroxy-24-oxocholesta-5,7-diene or the hydroxyl group-protected derivatives of formula (1), as mentioned above, is subjected at first to irradiation with ultraviolet rays in an inert organic solvent.

The ultraviolet rays having range in wave length from about 200 to 360 nm and were preferably from 260 to 310 nm are employed in the present invention, a hydrocarbon or halogenated hydrocarbon, such as hexane, heptane, cyclohexane, ligroin, benzene, toluene, xylene, bromobenzene, chlorobenzene, nitrobenzene, carbon tetrachloride, 1,2-dichloroethane, or 1,2-dibromoethane, an ether, such as diethyl ether, tetrahydrofuran, dioxane, methylcellosolve, or phenyl cellosolve, or an alcohol, such as methanol, ethanol, propanol, hexanol, or cyclohexanol, is preferably used.

The irradiation with ultraviolet rays is conducted in a temperature range from −20° to 80° C., preferably from −10° to 20° C. in an atmosphere free from oxygen, such as an argon or nitrogen atmosphere.

Thus, the irradiation with ultraviolet rays causes the cleavage between the 9- and 10-positions in the 5,7-diene compound used as a starting material to afford 1α-hydroxy-24-oxoprevitamin $D_3$ or a hydroxyl group-protected derivative thereof.

In the present invention the resulting previtamin $D_3$ is isomerized to 1α-hydroxy-24-oxovitamin $D_3$ or a hydroxyl group-protected vitamin $D_3$ of foregoing formula (2).

The temperature during the isomerization is not essentially important to the progress of the reaction itself. The equilibrium between the previtamin $D_3$ or a hydroxyl group-protected derivative thereof and the vitamin $D_3$ or a hydroxyl group-protected derivative thereof depends on the temperature and there are tendencies that the latter increases in proportions and at the same time the rate of the former converting into the latter slows down as the temperature falls. Therefore, the temperature can be chosen in consideration of the equilibrium value and conversion rate, and so, the temperature is not essentially important to the progress of the reaction itself.

On the basis of such consideration about the equilibrium value and conversion rate, a temperature of 10°–120° C. is practically adopted to the isomerization. Usually, the isomerization is preferably effected in an inert organic solvent, which is the same solvent as that used in the irradiation with ultraviolet rays in practical operation. The isomerization reaction is not necessarily required to be started after the completion of the reaction under the irradiation with ultraviolet rays, that is, after the stop of the irradiation, but the isomerization may be effected in parallel with the irradiation to convert the previtamin $D_3$ formed during the irradiation into the vitamin $D_3$. Thus, when 1α,3β-dihydroxy-24-oxocholesta-5,7-diene which is a compound of formula (1) wherein $R^1$ and $R^2$ are both hydrogen atoms, is used as a starting compound, 1α-hydroxy-24-oxovitamin $D_3$ of the formula (2) is prepared, and when a hydroxyl group-protected derivative wherein at least either one of $R_1$ or $R_2$, is a hydroxyl group protecting group, is used, 1α-hydroxy-24-oxovitamin $D_3$ is obtained by successive elimination of protecting group of hydroxyl group.

In the elimination of the protecting groups, when an acyl group is used as a protecting group, it is preferably cleaved in an alkaline alcohol such as NaOH-methanol or ethanol. The deacylation is preferably conducted in a temperature range from −10° to 50° C. for 30 minutes to 40 hours.

The protecting groups bonding with hydroxyl groups by ether linkages can be readily eliminated by contacting with an acid, such as diluted hydrochloric acid.

1α-Hydroxy-24-oxovitamin $D_3$ of formula (2) obtained as mentioned above can be isolated and purified by means of column chromatography, preparative thin layer chromatography, high pressure liquid chromatography or recrystallization.

The resultant 1α-hydroxy-24-oxovitamin $D_3$ has, as shown in animal tests described below, a high pharmaceutical action of promoting intestinal calcium absorption and raising the calcium concentration in blood.

Therefore, the 1α-hydroxy-24-oxyvitamin $D_3$ prepared in accordance with the present invention can be used as a drug applicable to diseases caused by abnormal calcium metabolism.

Suitable dosages of the novel 1α-hydroxy-24-oxovitamin $D_3$ in clinical application, based on the results of pharmacological tests conducted by the present inventors, have been found to be about 0.04–0.4 μg (about 96–960 p mole) per kilogram of the body weight of a warm-blooded animal.

The 1α-hydroxy-24-oxovitamin $D_3$ of the present invention can be clinically or veterinarily applied to the following diseases:

vitamin D dependent rickets, renal osteodystrophy, hypoparathyroidism, osteoporosis, osteomalacia, Behcet's disease, malabsorption syndrome, hypocalcemia induced by liver cirrhoss, hypocalcemia induced by steatorrhoea, hypocalcemia caused by vitamin D resistant rickets, and abnormal calcium and phosphorus metabolism caused by liver failure, renal failure, gastrointestinal tracts failure or parathyroid failure and related bone diseases.

Further, a composition containing the 1α-hydroxy-24-oxovitamin $D_3$ can be used in combination with other calcium metabolism regulating agents. For example, it can be applied to the treatment of Behcet's disease in combination with calcitonin.

Suitable routes of administration include oral, buccal, and parenterally any of intramuscular, subcutaneous, intravenous, and intrarectal. Dosage forms are, for example, compressed tablets, coated tablets, hard or soft elastic gelatin capsules, ethyl alcohol solutions, oil solutions, and aqueous suspensions.

The solvent for the oil solutions may be a vegetable oil such as corn, cotton seed, coconut, almond or peanut oil, a fish liver oil, or an oily ester such as polysorbate 80.

For intrarectal administration, the 1α-hydroxy-24-oxovitamin $D_3$ may be formed into a pharmaceutical composition containing a suppository base such as cacao butter or other triglycerides. To prolong the shelf life of the pharmaceutical composition, it may advantageously include an antioxidant such as ascorbic acid, butylated hydroxyanisole, or hydroquinone.

The 1α-hydroxy-24-oxovitamin $D_3$ of this invention can be mixed with a feed for domestic animals and the feed composition for domestic animals which contains the compound can be used in amounts not to cause toxicity for the prevention of hypocalcemia of cows at, or near, the time of delivery, or the prevention of hypocalcemia of domestic animals with no history of hypocalcemia. When such composition are administrated to poultry during oviposition, it is possible to prevent them from laying soft-shell eggs, which constitutes another characteristic feature of the 1α-hydroxy-24-oxovitamin $D_3$ of the present invention.

The following Examples illustrate the present invention in greater detail. It should be noted that these Examples do not in any way limit the scope of the invention.

The test methods used in these Examples for the determination of the characteristics of the products were as follows:

Unless otherwise specified, NMR spectra were determined by varian EM or JEOL PS/PFT-100 (Nippon Electronics Co., Ltd.) in deuterochloroform ($CDCl_3$) using tetramethylsilane as internal standard.

Mass spectra and high resolution mass spectra were determined by using shimadzu LKB-9000 (Shimadzu Seisakusho Co., Ltd.).

UV spectra were determined by Hitachi EPS-3T (Hitachi Limited) using an ethanol solution.

The melting point was measured by means of a hot stage microscope, and the resulting values were not corrected.

EXAMPLE 1

Ten (10) milligrams of 1α,3β-dihydroxy-24-oxocholesta-5,7-diene was dissolved in diethyl ether to prepare 500 ml of the solution, in which the diethyl ether was purified by distillation after deoxidation treatment. The solution was irradiated with ultraviolet rays for 2 minutes at 5° C. in an atmosphere of argon using a 200 W high pressure mercury lamp (Model 654A-36 Hanovia Company). A part of the solution was taken out and its UV spectrum was determined. An absorption of 262–263 nm was observed, which may be ascribable to a previtamine $D_3$. After completion of the reaction, ether was evaporated at room temperature under reduced pressure. Benzene (100 ml.) was added to the residue and the isomerization reaction was carried out by refluxing the mixture for 2 hours under an argon atmosphere. After the reaction, the benzene was distilled off under reduced pressure to afford 10 mg. of a pale yellow solid. The product was carefully separated by means of preparative thin-layer chromatography using a silica gel carrier containing silver nitrate (developed thrice with methanol-chloroform) to give bands which can be confirmed with ultraviolet rays. From the least polar band, 2.1 mg of a solid was obtained. The product had the following properties and was identified as 1α-hydroxy-24-oxovitamin $D_3$.

UV spectrum; $\lambda_{max}^{ethanol}$ (nm) 264 ($\epsilon$=18,300); $\lambda_{min}^{ethanol}$ (nm) 228

Mass (m/e); 414 (M+), 396 (M-18), 378 (M-18×2)

NMR ($CDCl_3$+Acetone $d_6$), δ (ppm);
 0.54 (3H, s, C-18, $CH_3$)
 1.1 (6H, d, J=7 Hz, 26, 27-$CH_3$),
 4.2 (1H, b, C-1-H or C-3-H),
 4.4 (1H, b, C-3-H or C-1-H),
 5.0 (1H, m, C-19-H),
 5.3 (1H, m, C-19-H),
 6.1 (1H, d, J=11 Hz, C-6 or C-7-H),
 6.4 (1H, d, J-11 Hz, C-6 or C-7-H), The symbols, s, d, b and m mean singlet, doublet, broad and multiplet respectively.

High resolution mass spectrum;
 Found=414.3132 (M+)
 Required=414.31338 ($C_{27}H_{42}O_3$)

From the most polar band, 3 mg of 1α,3β-dihydroxy-24-oxocholesta-5,7-diene was recovered.

EXAMPLE 2

A benzene solution (500 ml.) containing 13 mg. of 1α,3β-diacetoxy-24-oxocholesta-5,7-diene was prepared, in which the benzene was purified by distillation after deoxidation treatment. The solution was irradiated with ultraviolet rays for 2 minutes at 10° C. under an argon atmosphere (the device for emitting ultraviolet rays used was the same as in Example 1). After the completion of the reaction, the product was subjected to isomerization by refluxing benzene for 2.5 hours under an arogon atmosphere. After the reaction, the benzene was largely evaporated off. Three (3) milliliters of 5% potassium hydroxide-methanol solution and 3 ml. of benzene were added, and the resulting mixture was kept at room temperature for 24 hours under an argon atmosphere.

The reaction product was diluted with water and extracted with ethyl acetate. The ethyl acetate layer was washed repeatedly with water, dried, and the ethyl acetate was evaporated off under reduced pressure. The residue was separated and purified in the same manner as in Example 1 to afford 2.2 mg. of 1α-hydroxy-24-oxovitamin $D_3$ having the same properties as the product in Example 1 except for the high resolution mass spectrum which was a little different from that in Example 1.

The high resolution mass spectrum of the product was found to be 414.3140 (M+).

EXAMPLE 3

A diethyl ether solution (500 ml.) containing 15 mg. of 1α,3β-dibenzoyloxy-24-oxocholesta-5,7-diene was prepared. The solution was irradiated with ultraviolet rays for 1.5 minutes under an argon atmosphere. After the reaction the ether was evaporated off at room temperature under reduced pressure. Benzene (100 ml.) was added to the residue and the mixture was refluxed for 2 hours under an argon atmosphere to conduct the isomerization reaction. After the reaction, the benzen was largely evaporated off under reduced pressure and 20 ml. of 5% potassium hydroxide-methanol solution, 1 ml. of methanol and 1 ml. of benzene were added to the residue. The mixture was subjected to alcoholysis for 4 hours at 40° C., diluted with water and extracted with ethyl acetate.

The ethyl acetate layer was washed with aqueous sodium bicarbonate and water, dried over anhydrous sodium sulfate and the ethyl acetate was evaporated off under reduced pressure to afford a light yellow oily residue.

The product was separated and purified by means of preparative thin layer chromatography using a silica gel carrier containing silver nitrate in the same manner as in Example 1 to afford 1.8 mg. of 1α-hydroxy-24-oxovitamin D$_3$ having the following properties.

UV spectrum; $\lambda_{max}^{ethanol}$ (nm), 264 ($\epsilon$=18,500); $\lambda_{min}^{ethanol}$ (nm), 228

High resolution mass spectrum; 414.3129 (M+)

Other properties were found to be the same as those of the product in Example 1.

EXAMPLE 4

Twenty (20) milligrams of 1α,3β-dipivaloyl-24-oxocholesta-5,7-diene was dissolved in 500 ml. of a diethyl ether ethanol mixture (volume ratio=450:50) which was purified by distillation after deoxidation treatment. The solution was irradiated with ultraviolet rays for 2 minutes at 12° C. under an argon atmosphere. After the reaction, diethyl ether was evaporated off under reduced pressure, the residue was incorporated with 200 ml. of benzene and subjected to isomerization reaction under reflux for 2.5 hours. Then large parts of the benzene and ethanol were carefully evaporated off under reduced pressure to afford 20 mg. of an oily residue. This product was carefully separated by means of preparative thin-layer chromatography using silica-gel carrier containing silver nitrate (developed four times with methanol-chloroform) to isolate 3.8 mg. of a compound having an absorption peak in UV spectrum, $\lambda_{max}^{ethanol}$ (nm) 264 ($\epsilon$=17,000). The isolated product was mixed with 3 ml. of 5% potassium hydroxide-methanol solution and 3 ml. of benzene and the mixture was maintained at 35° C. for 24 hours under an argon atmosphere.

The reaction product was diluted with water and extracted with ethyl acetate. The ethyl acetate layer was repeatedly washed with water, dried and then the ethyl acetate was evaporated off under reduced pressure. The residue was separated and purified in the same manner as in Example 1 to afford 2.1 mg. of 1α-hydroxy-24-oxovitamin D$_3$ which had the same physical properties as those of the product in Example 1.

EXAMPLE 5

A diethyl ether solution (500 mg.) containing 10 mg. of 1α,3β-ditoluoyl-24-oxocholesta-5,7-diene was prepared. The solution was irradiated with ultraviolet rays for 50 seconds at 10° C. under an argon atmosphere. After the reaction, the diethyl ether was largely evaporated off under reduced pressure. Benzene (200 ml.) was added to the residue and the isomerization reaction was conducted by refluxing the benzene for 2.5 hours under an argon atmosphere. A large portion of the benzene was carefully evaporated off under reduced pressure, the residue was mixed with 1.5 ml. of 5% potassium hydroxide-methanol solution and 1.5 ml. of benzene and the mixture was kept for 19 hours at room temperature under an argon atmosphere. The product was subjected to extraction, separation and purification in the same manner as in Example 1 to afford 1.1 mg. of 1α-hydroxy-24-oxovitamin D$_3$ which has the same properties as those of the product in Example 1.

EXAMPLE 6

Twenty (20) milligrams of 1α,3β-di(trimethylsilyloxyl)-24-oxocholesta-5,7-diene was dissolved in 500 ml. of benzene. The solution was irradiated with ultraviolet rays for 2 minutes at 13° C. under an argon atmosphere. After the reaction successively the isomerization reaction was effected by refluxing the benzene for 2 hours under an argon atmosphere. A large portion of the benzene was evaporated off under reduced pressure, 40 ml. of ethyl acetate and 20 ml. of ice water containing a few drops of diluted hydrochloric acid were added to the residue, and the mixture was stirred violently.

The ethyl acetate layer was separated, washed repeatedly with water and dried and then the ethyl acetate was evaporated off under reduced pressure. The residue was treated in the similar way as in Example 1 to afford 0.9 mg. of 1α-hydroxy-24-oxovitamin D$_3$ having the same properties as those of the product in Example 1.

EXAMPLE 7

Effect of 1α-hydroxy-24-oxovitamin D$_3$ on the promotion of intestinal calcium absorption:

Weanling Wistar male rats were fed only with a vitamin D-deficient and low calcium diet (made by GBI Corp.) for four weeks. When avitaminosis D was observed, 0.25 μg/kg of 1α-hydroxy-24-oxovitamin D$_3$ a solution in 95% ethanol was intraperitoneally administrated to the rats. After prescribed hours the rats were killed, the duodenum was taken out and the calcium absorption was determined by means of the everted gut sac method. The incubation was conducted with the intestinal tract of about 5 cm length at 37° C. for 90 minutes under shaking 120 times per minute in the presence of oxygen. After the reaction, the radio activity levels of the incubation media outside and inside the everted gut sac were determined by placing 0.2 ml. of each incubation medium in a vial, adding 12 ml. of the cocktail containing a scintillator, and then measuring the radioactivity with a liquid scintillation counter. The ratio of a radioactivity of the serosal membrane side, that is, the inside of the everted gut sac, to that of the mucosal membrane side, that is, the outside incubation medium was used as an index of calcium absorption.

The compositions of the incubation medium and the cocktail were as follows:
Incubation medium;
  NaCl: 125 mM,
  Fructose: 10 mM,
  Tris(hydroxymethyl)aminomethan 30 mM,
  CaCl$_2$: 0.25 mM,
  $^{45}$CaCl$_2$: 10 μCi/l
Cocktail;
  Toluene: 1200 ml,
  Ethyl cellosolve: 800 ml,
  2,5-diphenyl oxazole: 8 g,
  2,2-p-phenylenebis(5-phenyloxazole): 300 mg.

The results are given in FIG. 1, wherein the result of a control and that of an example in which vitamin $D_3$ was administrated equal in amount to the 1α-hydroxy-24-oxovitamin $D_3$ are shown as refferences in addition to the result of the present invention. In every test five rats were used.

In FIG. 1, the marks of black dot ● show the result of the control; white dot ○, of vitamin $D_3$ administrated in a ratio of 2.5 μg/kg i.p.; and white triangle △, of 1α-hydroxy-24-oxovitamin $D_3$ in a ratio of 2.5 μg/kg i.p. Further, in FIG. 1, the examples marked with double stars  have a significant difference from the control by p<0.01 and with triple stars *, by p<0.001.

It is clearly seen from the results given in FIG. 1 that 1α-hydroxy-24-oxovitamin $D_3$ develops more rapidly the action to promote intestinal calcium absorption than vitamin $D_3$.

EXAMPLE 8

Bone calcium mobilizing activity of 1α-hydroxy-24-oxovitamin $D_3$

1α-hydroxy-24-oxovitamin $D_3$ was administrated intraperitoneally in a ratio of 2.5 μg/kg to rats which had been fed in the same way as in Example 7. Prescribed hours later, blood was taken from the rats and the calcium content in the plasma was determined. As the amount of the calcium absorbed from the intestines is negligible (the calcium content in the diet is 0.003%), the increase of the calcium level in the plasma can be considered to reflect the amount of the calcium mobilized from the bone tissues.

Figure 2:
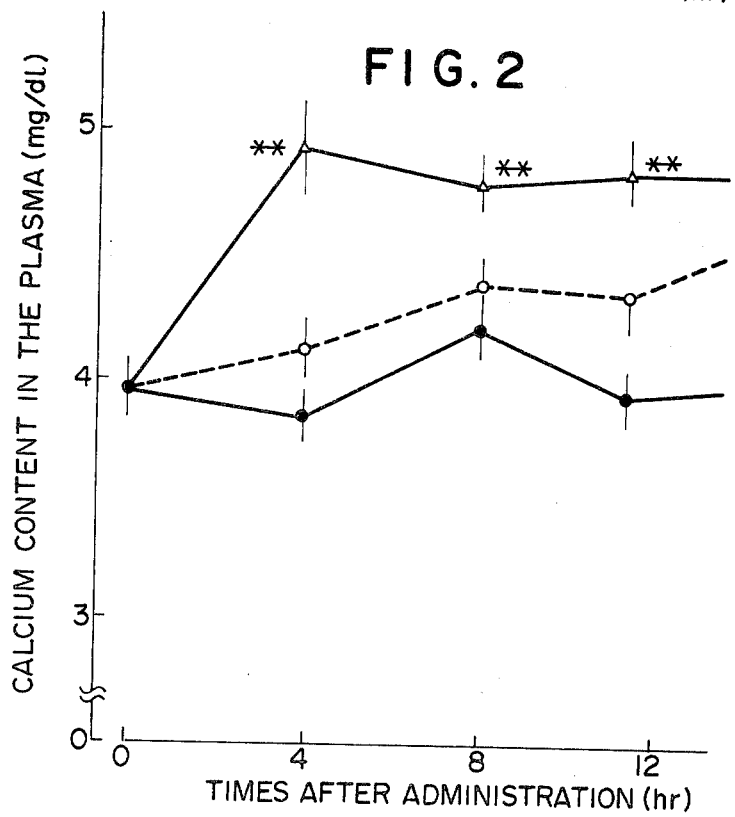

The results are given in FIG. 2, wherein the all marks express the same meanings as in Example 7 and five rats were used in every test. It is clearly seen from the results given in FIG. 2 that 1α-hydroxy-24-oxovitamin $D_3$ developes more rapidly the action to mobilize calcium from bone tissues than vitamin $D_3$.

As shown in the results of Examples 7 and 8, novel 1α-hydroxy-24-oxovitamin $D_3$ promotes the intestinal calcium absorption and calcium mobilization from bone in rats and these actions develope more rapidly than in vitamin $D_3$. This is a very important information in connection with the presumption that the 1α-hydroxy-24-oxovitamin $D_3$ of the present invention can be a precursor of 1α,24-dihydroxyvitamin D which fact was already reported by the present inventors, namely, the 24-oxo group is supposed to be converted to 24-hydroxyl group in vivo.

EXAMPLE 9

1α,3β-dihydroxy-24-oxocholesta-5,7-diene from 1α,3β-diacetoxy-24-oxocholesta-5,7-diene.

Twenty (20) milligrams of 1α,3β-diacetoxy-24-oxocholesta-5,7-diene prepared through the process described in U.S. Patent Application Ser. No. 906,785 was dissolved in 10 ml. of a 5% potassium hydroxide methanol solution and stirred at 40° C. overnight. After evaporation of methanol under reduced pressure, the residue was extracted thrice with 30 ml. of ethyl acetate. The separated ethyl acetate layers were combined and washed successively with 30 ml. of 1 N.HCl solution, 30 ml. of saturated aqueous NaHCO₃, and 30 ml. of saturated aqueous NaCl. After dried over Na₂SO₄ the solvent was evaporated off to give 16 mg. of a residue. The resulting product was purified by means of thin layer chromatography using kiesel gel 60 F254 (0.25 mm×20 cm×20 cm, Merck Co. Ltd.) and developing with benzene/aceton (5/1) to afford 14 mg. of a compound having the following physical properties.

UV spectrum $\lambda_{max}^{ethanol}$, n m; 261, 271, 282, 293.
NMR spectrum (CDCl₃); δ (ppm),
    0.63  (3H, s, 18-CH₃),
    0.95  (3H, s, 19-CH₃),
    1.08  (6H, d, J=7 Hz, 26, 27(CH₃)₂),
    3.7  (1H, m, 3α-H),
    4.1  (1H, m, 3α-H),
    5.38, 5.72 (1H, dd J=2 Hz, 6 Hz; 1H, d, J=6 Hz: 6, 7-Hs)
Mass spectrum (m/e):
    414 (M+), 396 (M-18), 378 (M-18×2)
High resolution mass spectrum:
    Found: 414.3136
    Required*, M+ (C₂₇H₄₂O₃) 414.3134

From the above properties, the product was identified as 1α,3β-dihydroxy-24-chloresta-5,7-diene.

EXAMPLE 10

1α,3β-dibenzoyloxy-24-oxocholesta-5,7-diene from 1α,3β-dihydroxy-24-oxocholesta-5,7-diene:

Twenty (20) mg. of 1α,3β-dihydroxy-24-oxocholesta-5,7-diene was dissolved in 2 ml. of dry pyridine and allowed to stand in a refrigerator (−20° C.) for 30 minutes. Then, 20 μl of benzoyl chloride was added thereto and allowed to stand in the refrigerator overnight. Then, 30 ml. of cold water was added thereto and extracted thrice with 30 ml. of ethyl acetate. The separated ethyl acetate layer was washed with 30 ml. of 1 N-HCl, 30 ml. of saturated NaHCO₃ aqueous solution and 18 ml. of water successively, and was dried over Na₂SO₄. The solvent was evaporated off under reduced pressure and 18 mg. of the residue was obtained. The residue was purified by means of thin layer chromatography using kieselgel 60 F254 (0.025 mm×20 cm×20 cm, Merck Co. Ltd.) and developing with benzene to afford a compound having the following properties:

UV spectrum $\lambda_{max}^{ethanol}$ (nm); 231, 261, 271, 282, 293.
NMR spectrum (CDCl₃, δ (ppm);
    0.62  (3H, s, 18-CH₃),
    1.08  (6H, d, J=7 Hz, 26-, 27-(CH₃)₂),
    4.95  (1H, m, 3α-H),
    5.32  (2H, m, 1β-H and 6- or 7-H),
    5.72  (1H, d, J=6 Hz, 6- or 7-H),
    7.49, 8.02  (10H, m, aromatic-2(H₅)),
Mass spectrum (m/e);
    622 (M+), 500 (M+-benzoic acid),
    378 (M+-2x benzoic acid),
High resolution mass spectrum;
    Found: 622.3651,
    Required, M+(C₄₁H₅₀O₅): 622.3658.

From the above properties, the compound was identified as 1α,3β-dibenzoyloxy-24-oxocholesta-5,7-diene.

EXAMPLE 11

1α,3β-bis(trimethylsilyloxy)-24-oxocholesta-5,7-diene from 1α,3β-dihydroxy-24-oxocholesta-5,7-diene:

200 mg. of 1α,3β-dihydroxy-24-oxocholesta-5,7-diene was dissolved in 1 ml. of N-trimethylsilylimidazole and allowed to stand in a refrigerator overnight. n-Hexane (50 ml.) was added thereto and washed thrice with 20 ml. of water. The n-hexane layer separated was dried over Na₂SO₄. The solvent was evaporated off under reduced pressure and 15 mg. of the residue was obtained. The product was purified by means of thin layer chromatography using kieselgel 60

F254 (0.25 mm×20 cm×20 cm, Merck Co. Ltd.) and developing with benzene to afford 5 mg. of a compound having the following properties:

UV spectrum $\lambda_{max}^{methanol}$ nm; 261, 271, 282, 293.

NMR spectrum (CDCl$_3$); $\epsilon$(ppm),

| | |
|---|---|
| 0.13 | (18H, s, trimethylsilyl —2(CH$_3$)$_3$), |
| 0.62 | (3H, s, 18—CH$_3$), |
| 0.90 | (3H, s, 19—CH$_3$), |
| 1.08 | (6H, d, J=7 Hz, 36, 27-(CH$_3$)$_2$), |
| 3.74 | (1H, m, 1$\beta$-H), |
| 4.02 | (1H, m, 3$\alpha$-H), |
| 5.34, 5.65 | (2H, a pair of m, 6-, 7-Hz) |

Mass spectrum (m/e): 558 (M+) 468 (m-trimethylsilyl)
378 (m-2×trimethylsilanol)

High resolution mass spectrum:

Found: 558.3923

Required, M+ (C$_{33}$H$_{58}$O$_3$Si$_2$): 558.3925

From above results, the compound was identified as 1$\alpha$, 3$\beta$-bis(trimethylsilyloxy)-24-oxocholesta-5,7-diene.

EXAMPLE 12

1$\alpha$,3$\beta$-bis(tetrahydropyranyloxy)-24-oxocholesta-5,7-diene from 1$\alpha$,3$\beta$-dihydroxy-24-oxocholesta-5,7-diene 20 mg. of 1$\alpha$,3$\beta$-dihydroxy-24-oxocholesta-5,7-diene was dissolved in 10 ml. of dry methylene chloride and 15 μl of distillated 2,3-dihydropyrane was added to the solution under cooling with ice-water. Then a catalyst amount of p-toluenesulfonic acid was added and stirred for 30 minutes. Methylene chloride (30 ml.) was added to the resulting mixture and washed with 20 ml. of saturated aqueous NaHCO$_3$ and 20 ml. of water and dried over Na$_2$SO$_4$. The solvent was evaporated off under reduced pressure and the residue was purified by means of thin layer chromatography using keiselgel 60 F254 (0.25 mm×20 cm×20 cm Merck Co. Ltd.) and developing with a solvent mixture of benzene and acetone (40:1) to afford 1.2 mg. of a compound having the following properties:

UV spectrum $\lambda_{max}^{ethanol}$, n m: 261, 271, 282, 293.

NMR spectrum ((CDCl$_3$), $\epsilon$(ppm)):

| | |
|---|---|
| 0.62 | (3H, s, 18—CH$_3$), |
| 0.94 | (3H, s, 19—CH$_3$), |
| 1.08 | (6H, d, J=7 Hz, 26, 27-(CH$_3$)$_2$), |
| 3.2–4.1 | (6H, m, 1$\beta$-, 3$\alpha$-Hz and 2 Hz at the 6-position of tetrahydropyranyl), |
| 4.73 | (2H, m, 2(H) at the 2-position of tetrahydropyranyl), |
| 5.35, 5.63 | (2H, a pair of m, 6-,7-Hz) |

High resolution mass spectrum:

Found: 582.4299

Required M+(C$_{37}$H$_{58}$O$_5$): 582.4284

From above properties, this compound was identified as 1$\alpha$,3$\beta$-bis(tetrahydropyranyloxy)-24-oxocholesta-5,7-diene.

REFERENCE 1

Preparation of 1$\alpha$,24-dihydroxyvitamin D$_3$ from 1$\alpha$-hydroxy-24-oxovitamin D$_3$ in the present invention (a) After 20 mg. of 1$\alpha$-hydroxy-24-oxovitamin D$_3$ had been dissolved in 20 ml. of tetrahydrofuran, 15 mg. of lithium aluminum hydride was added to the solution at room temperature (15 C.) and stirred for 3 hours under an argon atmosphere. After the reaction a small amount of diethyl ether saturated with water was added to the reaction mixture to decompose excess lithium aluminum hydride. Then the mixture was dried over anhydrous magnesium sulfate and the tetrahydrofuran was carfully evaporated off under reduced pressure. The resulting residue was purified by means of preparative thin layer chromatography (developing with 6% methanol-chloroform) to afford 18 mg. of 1$\alpha$,24-dihydroxyvitamin D$_3$ having the following properties:

UV spectrum: $\lambda_{max}^{ethanol}$ (nm), 265 ($\epsilon$=18,000); $\lambda_{min}^{ethanol}$ (nm), 228, NMR Spectrum (C$_3$D$_6$O); $\delta$(ppm),

| | |
|---|---|
| 0.57 | (6H, d, 18-CH$_3$-), |
| 0.87 | (6H, d, J=7 Hz, 26-,27-CH$_3$), |
| 0.96 | (3H, d, J=5 Hz 21-CH$_3$), |
| 3.19 | (1H, m, 24-H), |
| 4.15 | (1H, m, 16-H), |
| 4.36 | (1H, m, 3$\alpha$-H), |
| 4.85 | (1H, bs, 19-H), |
| 5.30 | (1H, bs, 19-H), |
| 6.05 | (1H, d, J$_{AB}$=11 Hz, 6 or 7-H), |
| 6.25 | (1H, d, J$_{AB}$=11 Hz, 6 or 7-H). |

Mass spectrum (m/e);

416 (M+), 398, 380, 269, 251, 134.

High resolution mass spectrum:

M+ (C$_{27}$H$_{44}$O$_3$)=416.32927

Found: 416.32768

Melting point; 84°–85° C.

(b) 18 mg. of 1$\alpha$,3$\beta$-diacetoxy-24-oxovitamin D$_3$ (1$\alpha$-acetoxy-24-oxocholecalciferol 3$\beta$-acetate) was dissolved in 20 ml. of methanol and 15 mg. of sodium borohydride was added to the solution at room temperature under an argon atmosphere. Stirring was continued for 10 hours at room temperature. After the reaction, a small amount of 10% acetic acid solution was added to decompose the excess sodium borohydride and the methanol was evaporated off under reduced pressure. The residue was purified by means of preparative thin layer chromatography to afford 14 mg. of 1$\alpha$-acetoxy-24-hydroxyvitamin D$_3$ 3$\beta$-acetate. The properties of the product were as follows:

UV spectrum; $\lambda_{max}^{ethanol}$(nm), 264 ($\epsilon$=18,600); $\lambda_{min}^{ethanol}$(nm), 228.

Further, 12 mg. of the above 1$\alpha$-acetoxy-24-hydroxyvitamin D$_3$ 3$\beta$-acetate was dissolved in 2 ml. of benzene, a 5% potassium hydroxide-methanol solution was added and the resulting mixture was allowed to stand at room temperature for 20 hours. After the reaction, the reaction mixture was diluted with water and extracted with ethyl acetate. The ethyl acetate layer was repeatedly washed with water, dried over sodium sulfate and the ethyl acetate was evaporated off under reduced pressure. The residue was separated and purified by means of thin layer chromatography to afford 8 mg. of 1$\alpha$,24-dihydroxyvitamin D$_3$, which had the same physical properties as those of the product obtained in (a).

(c) 20 mg. of 1$\alpha$,3$\beta$-dibenzoyloxy-24-oxovitamin D$_3$ was dissolved in 25 ml. of methanol and 18 mg. of sodium borohydride was added to the solution at room temperature under an argon atmosphere. Stirring was continued for 10 hours. After the reaction a small amount of 10% acetic acid was added to decompose the excess sodium borohydride and the methanol was evaporated off under reduced pressure. The residue was purified by means of preparative thin layer chromatography to afford 15 mg. of 1$\alpha$,3$\beta$-dibenzoyloxy-24-hydroxyvitamin D$_3$.

The product was dissolved in 5 ml. of 7% possium hydroxide-methanol solution and allowed to stand for 18 hours at room temperature. The mixture was diluted with water and extracted with ethyl acetate. The ethyl acetate layer was washed repeatedly with 5% aqueous sodium hydroxide and water, dried over sodium sulfate and the ethyl acetate was evaporated off under reduced pressure. The resultant residue was separated and purified by means of thin layer chromatography to afford 9.8 mg. of 1α,24-dihydroxy-vitamin D3 having the same physical properties as those of the product in above reference 1 (a).

REFERENCE 2

An example of the preparation of 1α,3β,24-trihydroxycholesta-5,7-diene or the hydroxyl group-protected derivatives thereof, which are intermediates of 1α,24-dihydroxyvitamin D3 (U.S. Pat. No. 4,022,891), from 1α,3β-dihydroxy-24-oxocholesta-5,7-diene or the hydroxyl group-protected derivatives thereof in the present invention.

(a) 15 mg. of 1α,3β-dihydroxy-24-oxocholesta-5,7-diene was dissolved in 38 ml. of methanol and 15 mg. of sodium borohydride was added to the solution at room temperature under an argon atmosphere. Stirring was continued for 8 hours at 30° C., a small amount of 10% aqueous acetic acid was added to decompose the excess sodium borohydride and the methanol was evaporated off under reduced pressure. The residue was separated and purified by means of preparative thin layer chromatography (developing with 6% methanol-chloroform) to afford 11 mg. of 1α,3β,24-trihydroxycholesta-5,7-diene having the following physical properties:

UV spectrum, $\lambda_{max}^{ethanol}$(nm): 262, 271 ($\epsilon=11,000$), 282 ($\epsilon=12,000$), 294 ($\epsilon=7,000$), NMR spectrum (in $C_3D_6O$):
- 0.63 (3H, s, 18-$CH_3$),
- 3.30 (1H, m, 24-H),
- 3.70 (1H, m, 1β-H),
- 4.08 (1H, m, 3α-H),
- 5.30 (1H, d, J=6 Hz, 6 or 7-H),
- 5.60 (1H, d, J=6 Hz, 6 or 7-H), Mass spectrum (m/e): 416 (M+), 398, 380, 357, 251, 227, 197, 157, Melting point: 102°–103° C.

(b) 25 mg. of 1α,3β-diacetoxy-24-oxocholesta-5,7-diene was dissolved in 25 ml. of tetrahydrofuran, 15 mg. of lithium aluminum hydride was added to the solution at room temperature and stirring was continued for 2.5 hours under an argon atmosphere. After the reaction a small amount of diethyl ether saturated with water was added to decompose the excess lithium aluminum hydride, the mixture was dried over anhydrous magnesium sulfate and then the tetrahydrofuran was carefully evaporated off under reduced pressure.

The residue was purified by means of preparative thin layer chromatography (developing with 6% methanol-chloroform to afford 18 mg. of 1α,3β,24-trihydroxycholesta-5,7-diene having the same physical properties as those of the product obtained in the above reference 2(a).

(c) 20 mg. of 1α,3β-diacetoxy-24-oxocholesta-5,7-diene was dissolved in 25 ml. of methanol and 20 mg. of sodium borohydride was added to the solution at room temperature under an argon atmosphere. Stirring was continued for 8 hours at 35° C., then a small amount of 10% aqueous acetic acid was added to decompose the excess sodium borohydride, and methanol was evaporated off under reduced pressure. The residue was separated by means of preparative thin layer chromatography (developing with 3% methanol-chloroform) to afford 15 mg. of 1α,3β-diacetoxy-24-hydroxycholesta-5,7-diene having the following physical properties:

UV spectrum, $\lambda_{max}^{ethanol}$(nm): 261, 271 ($\epsilon=11,200$), 282 ($\epsilon=12,000$), 293.

NMR spectrum (in $C_3D_6O$):
- 0.63 (3H, s, 18-$CH_3$)
- 2.03 (6H, s, $CH_3COO-$),
- 3.30 (1H, m, C-24-H),
- 4.75 (1H, b, C-3-H),
- 5.01 (1H, b, C-1-H),
- 5.35 (1H, d, J=6 Hz, C-6 or C-7-H),
- 5.69 (1H, d, J=6 Hz, C-6, or C-7-H). Further, 10 mg. of the diacetate derivative was dissolved in 10 ml. of 10% potassium hydroxide-methanol solution and stirred for 18 hours at room temperature. After the reaction, the mixture was diluted with water and extracted with ethyl acetate. The ethyl acetate layer was washed repeatedly with water, dried over anhydrous sodium sulfate and then the ethyl acetate was evaporated off under reduced pressure.

The residue was separated and purified by means of preparative thin layer chromatography to afford 6 mg. of 1α,3β,24-trihydroxycholesta-5,7-diene having the same physical properties as those of the product in Reference 2(a).

(d) 18 mg. of 1α,3β-dibenzoyloxy-24-oxocholesta-5,7-diene was dissolved in 20 ml. of tetrahydrofuran, 18 mg. of lithium aluminum hydride was added to the solution at room temperature and stirring was continued for 5 hours under an argon atmosphere.

After the reaction, a small amount of diethyl ether saturated with water was added to the mixture to decompose the excess lithium aluminum hydride, the mixture was dried over anhydrous magnesium sulfate, and tetrahydrofuran was carefully evaporated off under reduced pressure. The resulting residue was purified by preparative thin layer chromatography (developing with 6% methanol-chloroform) to afford 10 mg. of 1α,3β,24-trihydroxycholesta-5,7-diene with the same physical properties as those of the products obtained in Reference 2, (a).

What is claimed is:

1. 1α-Hydroxy-24-oxovitamin D3.

2. 1α,3β-Dihydroxy-24-oxocholesta-5,7-diene or the derivatives thereof represented by the following formula (1-a):

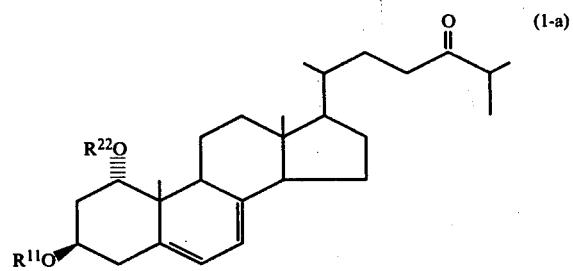

wherein $R^{11}$ and $R^{22}$ are same or different and represent hydrogen atom, acyl group of at least three carbon atoms, trialkylsilyl group, or 2-cyclic ether group.

3. 1α,3β-Dihydroxy-24-oxocholesta-5,7-diene.

4. A pharmaceutically effective composition for warm-blooded animals comprising a pharmaceutically effective amount of 1α-hydroxy-24-oxovitamin D3.

5. A pharmaceutical composition for warm-blooded animals according to claim 4 which is administrable orally or by intramuscular or intravenous injection, said composition comprising a pharmaceutically effective amount of 1α-hydroxy-24-oxovitamin $D_3$ and a vehicle non-toxic to warm-blooded animals.

6. A pharmaceutical composition for controlling calcium metabolism of warm-blooded animals according to claim 4 or 5, which comprises a pharmaceutically effective amount of 1α-hydroxy-24-oxovitamin $D_3$ and a vehicle non-toxic to warm-blooded animals.

7. A method for controlling the calcium metabolism of warm-blooded animals, which comprises administering a pharmaceutically effective amount of 1α-hydroxy-24-oxovitamin $D_3$ orally, subcutaneously, intramuscularly or intravenously.

* * * * *